United States Patent [19]

Infinger et al.

[11] Patent Number: 5,350,402
[45] Date of Patent: Sep. 27, 1994

[54] ATRIAL DEFIBRILLATOR AND METHOD FOR PROVIDING T WAVE DETECTION AND INTERVAL TIMING PRIOR TO CARDIOVERSION

[75] Inventors: Kenneth R. Infinger, Redmond; Gregory M. Ayers, Duvall; Darrell O. Wagner, Gold Bar; John M. Adams, Issaquah, all of Wash.

[73] Assignee: InControl, Inc., Redmond, Wash.

[21] Appl. No.: 67,688

[22] Filed: May 26, 1993

[51] Int. Cl.$^5$ .............................. A61N 1/39
[52] U.S. Cl. ............................................. 607/5
[58] Field of Search ........................... 607/4, 5, 6, 7

[56] References Cited

U.S. PATENT DOCUMENTS 5,205,283  4/1993  Olson ................................. 607/5
5,269,298  12/1993  Adams et al. ...................... 607/5

*Primary Examiner*—Kyle L. Howell
*Assistant Examiner*—George Manuel
*Attorney, Agent, or Firm*—Foley & Lardner

[57] ABSTRACT

An implantable atrial defibrillator and method provides cardioverting electrical energy to the atria of a human heart in need of cardioversion. The atrial defibrillator includes a first detector for detecting R waves of the heart, a second detector for detecting T waves of the heart, and a third detector for detecting atrial activity of the heart. An atrial fibrillation detector is responsive to the third detector for determining when the atria of the heart are in need of cardioversion. A cardioverting stage applies the cardioverting electrical energy to the atria of the heart when the atria of the heart are in need of cardioversion, after the second detector detects a T wave, and in timed relation to an R wave detected by the first detector after the detected T wave is completed. The atrial defibrillator includes a timer for timing a predetermined delay time after the T wave is detected, which delay time must be completed before the atria are cardioverted in timed relation to a detected R wave to assure that the detected T wave is completed.

26 Claims, 2 Drawing Sheets though it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

ATRIAL DEFIBRILLATOR AND METHOD FOR PROVIDING T WAVE DETECTION AND INTERVAL TIMING PRIOR TO CARDIOVERSION

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may result from the mistimed delivery of cardioverting electrical energy to the atria of the heart. More specifically, the atrial defibrillator of the present invention guards against applying cardioverting electrical energy to the atria of the heart under conditions believed to contribute to induced ventricular fibrillation.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved atrial defibrillators and lead systems which exhibit both automatic operation and improved safety are fully described in copending U.S. applications Ser. No. 07/685,130, filed Apr. 12, 1991, in the names of John M. Adams and Clifton A. Alferness for IMPROVED ATRIAL DEFIBRILLATOR AND METHOD and Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. As disclosed in the aforementioned referenced applications, synchronizing the delivery of the defibrillating or cardioverting electrical energy to the atria with a ventricular electrical activation (R wave) of the heart is important to prevent induced ventricular fibrillation. Ventricular fibrillation is a fatal arrhythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection assure reliable synchronization.

Another measure for reducing the risk of inducing ventricular fibrillation during the delivery of cardioverting electrical energy to the atria of the heart employed by the defibrillators of the aforementioned referenced applications is the reduction of the amount of the electrical energy which is passed through the ventricles during cardioversion of the atria. This is achieved by locating the cardioverting electrodes in or near the heart to provide a cardioverting energy path which confines most of the cardioverting electrical energy to the atria of the heart.

The atrial defibrillator and method of the present invention provides improved safety and reduction in the risk of inducing ventricular fibrillation during atrial cardioversion or defibrillation. It has been observed that during episodes of atrial fibrillation, the cardiac rate increases to a high rate and/or becomes extremely variable. At high cardiac rates, the R wave of each cardiac cycle becomes closely spaced from the T wave of the immediately preceding cardiac cycle. This may lead to a condition known in the art as an "R on T" condition which is believed to contribute to induced ventricular fibrillation if the atria are cardioverted in synchronism with the R wave close to the T wave. During highly variable cardiac rates, a long cardiac cycle can be followed by a relatively short cardiac cycle. This condition in conjunction with a high cardiac rate is believed to cause a dispersion of refractoriness and also can result in an increased vulnerability to ventricular fibrillation. For a more complete understanding of the aforementioned highly variable cardiac rate and the consequences thereof, reference may be had to an article entitled El-Sherif et al., Reentrant Ventricular Arrhythmias in the Late Myocardial Infarction Period: Mechanism by Which a Short-Long-Short Cardiac Sequence Facilitates the Induction of Reentry, *Circulation*, 83(1):268–278 (1991).

U.S. Pat. No. 5,207,219, which issued on May 4, 1993 in the names of John M. Adams, Clifton A. Alferness, Kenneth R. Infinger, and Joseph M. Bocek, entitled ATRIAL DEFIBRILLATOR AND METHOD FOR PROVIDING INTERVAL TIMING PRIOR TO CARDIOVERSION, and which is assigned to the assignee of the present invention, discloses an atrial defibrillator and method which greatly reduces the risk of inducing ventricular fibrillation during atrial cardioversion or defibrillation by avoiding applying the cardioverting electrical energy to the atria at those instances when increased vulnerability to ventricular fibrillation may be present. As disclosed in that patent, this is accomplished by interval timing prior to applying the cardioverting or defibrillating electrical energy. The time interval between immediately successive R waves is timed and the cardioverting or defibrillating electrical energy is only applied when a timed interval is greater than a preselected minimum interval. This provides protection from the increased vulnerability to ventricular fibrillation condition resulting from a high cardiac rate. To provide further protection for the R on T condition resulting from a highly variable cardiac rate, an additional condition may be applied to the timed interval requiring the timed interval to also be less than a preselected maximum interval before the cardioverting or defibrillating energy is applied to the atria.

The present invention provides an alternative approach to that disclosed in U.S. Pat. No. 5,207,219. The atrial defibrillator and method of the present invention also guards against applying the cardioverting electrical energy to the atria when increased vulnerability to ventricular fibrillation may be present.

SUMMARY OF THE INVENTION

The present invention therefore provides an atrial defibrillator for providing cardioverting electrical energy to the atria of a human heart. The atrial defibrillator includes detecting means for detecting R waves and T waves of the heart and cardioverting means responsive to the detecting means for applying the cardioverting electrical energy to the atria of the heart after a T wave is detected by the detecting means and in timed relation to an R wave detected by the detecting means after the detected T wave is completed. The R wave detected after the detected T wave is completed is the first R wave detected after the detected T wave.

The present invention further provides an implantable atrial defibrillator for providing cardioverting electrical energy to the atria of a human heart in need of cardioversion. The atrial defibrillator includes first detecting means for detecting R waves of the heart, second detecting means for detecting T waves of the heart, and third detecting means for detecting atrial activity of the heart. The atrial defibrillator further includes atrial fibrillation detecting means responsive to the third detecting means for determining when the atria of the heart are in need of cardioversion, and cardioverting means for applying the cardioverting electrical energy to the atria of the heart when the atria of the heart are in need of cardioversion, after the second detecting means detects a T wave, and in timed relation to an R wave detected by the first detecting means after the detected T wave is completed. The R wave detected after the detected T wave is completed is the first R wave detected by the first detecting means after the detected T wave.

The present invention still further provides a method of applying cardioverting electrical energy to the atria of a human heart in need of cardioversion. The method includes the steps of detecting T waves of the heart, detecting R waves of the heart, and applying the cardioverting electrical energy to the atria of the heart in timed relation to the first R wave detected following a detected and completed T wave.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION. OF THE PREFERRED EMBODIMENT

Figure 1:
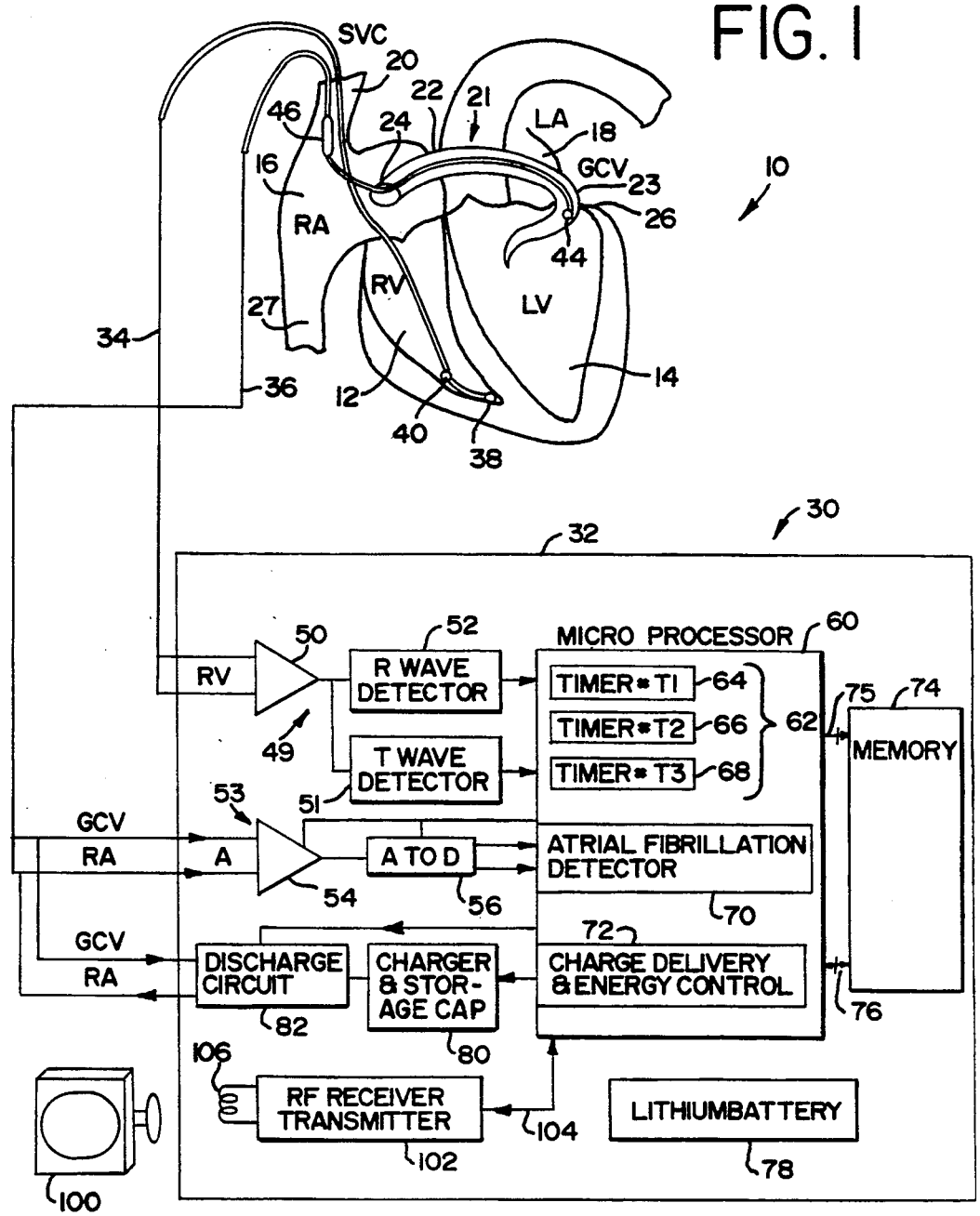
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "ventricular activations" denotes R waves of the heart cardiac cycle which are depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of R waves and T waves of the heart 10 in the right ventricle. As illustrated, the lead 34 is preferably fed through the superior vena cava 20, into the right atrium 16, and then into the right ventricle 12 as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This reduces the potential for ventricular fibrillation of the heart to be induced as a result of the application of defibrillating electrical energy of the atria of the heart.

Within the enclosure 32, the atrial defibrillator 30 includes detecting means 49 including a T wave detector 51, a first sense amplifier 50, and an R wave detector 52. The inputs of sense amplifier 50 are coupled to electrodes 38 and 40 respectively of lead 34 for sensing electrical activity of the heart 10 in the right ventricle 12. The electrocardiogram (ECG) output of the sense amplifier is fed to both the R wave detector 52 and T wave detector 51. The R wave detector 52 forms a first detecting means which, responsive to the output of sense amplifier 50, detects R waves of the heart 10. The T wave detector 51 forms a second detecting means which, responsive to the output of sense amplifier 50, detects T waves of the heart 10. The R wave detector 52 and T wave detector 51 may be of the type known in the art. However, since both R waves and T waves are detected, it is preferable that the R wave detector 52 and T wave detector 51 have different detection characteristics so that a detected R wave is not confused with a detected T wave and vice versa.

The enclosure 32 further includes a second sense amplifier 54 which is coupled to an analog to digital converter 56. The inputs of sense amplifier 54 are coupled to electrodes 44 and 46 respectively of lead 36 to form a third detecting means 53 for detecting atrial activity of the heart 10. The output of sense amplifier 54 provides an analog output representative of the atrial activity of the heart 10 which is fed to the analog to digital converter 56. The analog to digital converter 56 converts the analog signal representative of the atrial activity of the heart being detected to digital samples for further processing in a manner to be described hereinafter.

The enclosure 32 of the atrial defibrillator 30 further includes a microprocessor 60. The microprocessor 60 is preferably implemented in a manner as disclosed in the aforementioned copending U.S. application, Ser. Nos. 07/685,130 and 07/856,514 and further as described hereinafter with respect to the flow diagram of FIG. 2. The implementation of the microprocessor 60 in accordance with this embodiment of the present invention results in a plurality of functional stages. The stages include a timing means 62 including a first timer 64, a second timer 66 and a third timer 68, an atrial arrhythmia detector in the form of an atrial fibrillation detector 70, and a charge delivery and energy control stage 72.

The microprocessor 60 is arranged to operate in conjunction with a memory 74 which may be coupled to the microprocessor 60 by a multiple-bit address bus 75 and a bi-directional multiple-bit data bus 76. This permits the microprocessor 60 to address desired memory locations within the memory 74 for executing write or read operations. During a write operation, the microprocessor 60 stores data, such as time intervals or operating parameters in the memory at the addresses defined by multiple-bit addresses conveyed over the address bus 75 and conveys the data to the memory 74 over the multiple-bit data bus 76. During a read operation, the microprocessor 60 obtains data from the memory 74 at the storage locations identified by the multiple-bit addresses provided over the address bus 75 and receives the data from the memory over the bi-directional data bus 76.

For entering operating parameters into the microprocessor 60, the microprocessor 60 receives programmable operating parameters from an external controller 100 which is external to the skin of the patient. The external controller 100 is arranged to communicate with a receiver/transmitter 102 which is coupled to the microprocessor 60 over a bi-directional bus 104. The receiver/transmitter 102 may be of the type well known in the art for conveying various information which it obtains from the microprocessor 60 to the external controller 100 or for receiving programming parameters from the external controller 100 which the receiver/transmitter 102 then conveys to the microprocessor 60 for storage in internal memory (not shown) or in the aforementioned external memory 74 within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 80 of the type well known in the art which charges a storage capacitor to a predetermined voltage level and a discharge circuit 82 for discharging the storage capacitor within circuit 80 to provide a discharge output of electrical energy when required to the atria of the heart. To that end, the discharge circuit 82 is coupled to the first electrode 44 and the second electrode 46 of the second lead 36 for applying the cardioverting or defibrillating electrical energy to the atria. Lastly, the defibrillator 30 includes a depletable power source 78, such a lithium battery, for providing power to the electrical components of the atrial defibrillator 30.

The sense amplifier 50 and the R wave detector 52 continuously detect the occurrence of R waves (ventricular activations) of the right ventricle 12. As disclosed in the aforementioned copending U.S. application Ser. Nos. 07/685,130 and 07/856,514, herein incorporated by reference, when the time intervals between immediately successive R waves indicate the probability of an episode of atrial fibrillation, the microprocessor 60 enables the atrial fibrillation detector 70, sense amplifier 54, and the analog to digital converter 56. If the atrial fibrillation detector 70 determines that the atria 16 and 18 are in fibrillation and thus in need of cardioversion, the charge delivery control 72 causes the charger and storage capacitor circuit 80 to charge the storage capacitor within circuit 80. The operation of the atrial defibrillator 30 then enters the implementation illustrated in the flow diagram of FIG. 2.

Figure 2:
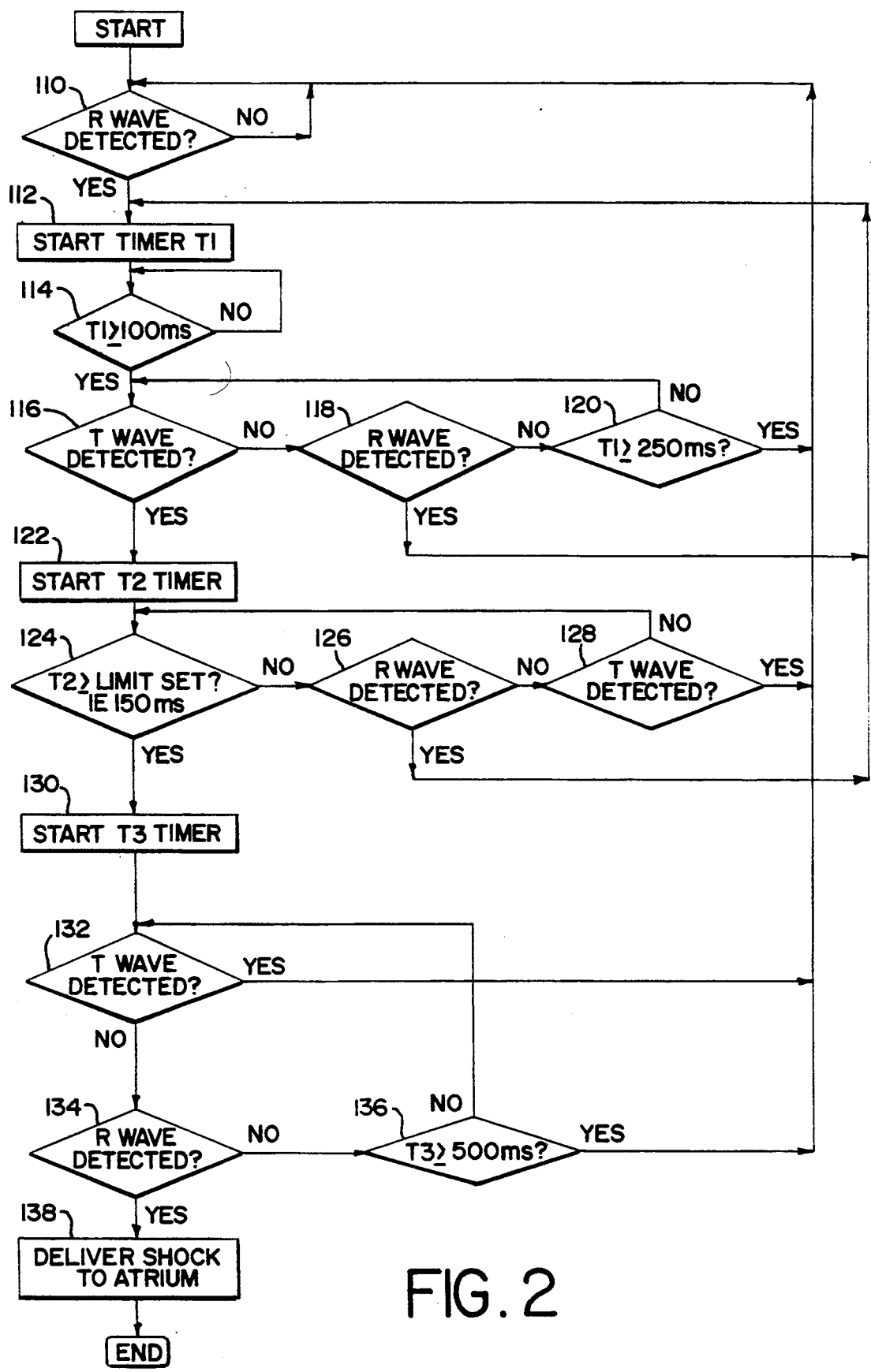
FIG. 2 is a flow diagram illustrating the manner in which the atrial defibrillator of FIG. 1 may be implemented in accordance with the present invention for applying defibrillating or cardioverting electrical energy to the atria of the heart with reduced risk of inducing ventricular fibrillation.

Referring now to FIG. 2, the microprocessor 60 first, in step 110, determines if an initial R wave has been detected by sense amplifier 50 and the R wave detector 52. If an initial R wave has not been detected, the microprocessor returns. If an initial R wave has been detected, the microprocessor then in step 112 resets to zero and starts the first timer 64 for timing a first predetermined time period. The duration of the first predetermined time period is preferably selected to have a time interval corresponding to the time interval following the detection of the initial R wave in step 110 in which a T wave would be expected to occur. As an example, the first predetermined time period may have a duration of 250 milliseconds.

Once the first timer 64 is started in step 112, the microprocessor 60 then in step 114 waits for a period of 100 milliseconds. Hence, in step 114, as long as the microprocessor determines that the time on the first timer 64 is less than 100 milliseconds, the microprocessor repeats step 114. When the time on the first timer 64 reaches 100 milliseconds, the microprocessor proceeds to step 116 to determine if a T wave is being detected by the T wave detector 51. If a T wave is not being detected, the microprocessor proceeds to step 118 to determine if an R wave is being detected by the R wave detector 52. If an R wave is not being detected in step 118, the microprocessor then proceeds to step 120 to determine if the timer 64 has completed the timing of the first predetermined time period. If the first timer 64 has not completed the timing of the first predetermined time period, the microprocessor returns to step 116 to once again determine if a T wave is being detected by the T wave detector 51.

If in step 118 it is determined that an R wave is being detected prior to the first timer 64 completing the timing of the first predetermined time period, the microprocessor will return to restart the first timer 64 and thus to restart the timing of the first predetermined time period. Hence, the first timer 64 is responsive to the R wave detector 52 detecting an R wave within the first predetermined time period for retiming the first predetermined time period. This step is provided in case two successive R waves are detected without an intervening T wave being detected within the first predetermined time period. If such an R wave is detected in step 118 prior to the first timer 64 completing the timing of the first predetermined time period, the R wave detected in step 118 then becomes the initial detected R wave.

If in step 120 it is determined that the first timer 64 has completed the timing of the first predetermined time period, the microprocessor then returns to step 110 for detecting a further initial R wave. Hence, the R wave detector 52 is responsive to the first timer 64 completing the timing of the first predetermined time period without a T wave or an R wave being detected to detect for a further initial R wave.

If in step 116 a T wave is detected before timer 64 completes the timing of the first predetermined time period, the microprocessor then resets to zero and starts the second timer 66 in step 122. The second timer 66 times a predetermined delay time to assure that the T wave detected in step 116 is completed prior to the application of the cardioverting electrical energy to the atria of the heart in synchronism with the next detected R wave. The predetermined delay time may have a duration, for example, of 150 milliseconds. Hence, the second timer 66 only times the predetermined delay time when the T wave detector 51 detects a T wave within said first predetermined time period.

The microprocessor, after starting the second timer 66, proceeds to step 124 to determine if the second timer 64 has completed the timing of the predetermine delay time. If the second timer 66 has not completed the timing of the predetermined delay time, the microprocessor then proceeds to step 126 to determine if an R wave is being detected. If an R wave is being detected, the microprocessor returns to step 112 to restart the first timer 64. As a result, the R wave detected in step 126 will become the initial detected R wave. Hence, the first timer 64 is responsive to the R wave detector 52 detecting an R wave within the predetermined delay time for retiming the first predetermined time period.

If an R wave is not being detected in step 126, the microprocessor proceeds to step 128 to determine if a subsequent T wave is being detected. If a T wave is being detected in step 128, the microprocessor returns to step 110 for detecting a further initial R wave. Hence, the R wave detector 52 is responsive to the second timer 66 and to the T wave detector 51 detecting a further T wave during the predetermined delay time to detect for a further initial R wave. The implementation of step 128 assures that an R wave is not mistaken for a T wave detected in step 116.

If the second timer 66 completes the timing of the predetermined delay time without an R wave being detected in step 126 or a T wave being detected in step 128, the microprocessor then proceeds to step 130 for resetting to zero and starting the third timer 68. The third timer 68 times up to a predetermined time period which is selected, as will be seen hereinafter, to assure that the current cardiac cycle is not excessively long. As previously mentioned, during atrial fibrillation, the heart rate may be highly variable resulting in increased vulnerability for inducing ventricular fibrillation. If the current cardiac cycle is too long, it may be followed by a short cardiac cycle resulting in increased vulnerability. As a result, with the third timer 68 timing up to a predetermined time period, a further condition is imposed prior to cardioversion. This further condition requires that the current cardiac cycle not be excessively long. The duration of the predetermined time period up to which the third timer 68 times may be, for example, 500 milliseconds.

After the third timer 68 is started, the microprocessor in step 132 determines if a T wave is being detected. If a T wave is being detected in step 132, the microprocessor returns to step 110 to detect for a further initial R wave. Hence, the R wave detector 52 is responsive to the T wave detector 51 detecting a further T wave before detecting the first R wave following the T wave detected in step 116 to detect for a further initial R wave.

If a T wave is not being detected in step 132, the microprocessor then proceeds to step 134 to determine if an R wave is being detected. If an R wave is not being detected in step 134, the microprocessor then proceeds to step 136 to determine if the third timer 68 has completed the timing of the predetermined time period. If the third timer 68 has completed the timing of the predetermined time period, the microprocessor returns to step 110 to detect for a further initial R wave. As a result, the R wave detector 52 is responsive to the third timer 68 completing the timing of the predetermined time period without detecting the first R wave following the T wave detected in step 116 to detect for a further initial R wave. If in step 136 the third timer 68 has not completed the timing of the predetermined time period, the microprocessor returns to step 132.

If in step 134 the microprocessor determines that an R wave is being detected, the charge delivery and energy control 72 then causes the discharge circuit 82 to apply the cardioverting electrical energy to electrodes 44 and 46 and thus to the atria of the heart in step 138 in synchronism with the R wave detected in step 134. As a result, the cardioverting electrical energy is applied to the atria after a T wave is detected by the T wave detector 51 in step 116 and in timed relation to an R wave detected in step 134 wherein the R wave detected in step 134, by virtue of the predetermined delay time timed by the second timer 66, occurs and is detected at a time after the T wave detected in step 116 is completed to assure that the cardioverting electrical energy is not applied to the atria at a time when the heart is vulnerable to induced ventricular fibrillation. As will be further noted, the R wave detected in step 134 is the first R wave detected after the completed T wave detected in step 116.

As will also be noted in FIG. 2, when it is determined that the third timer 68 has completed the timing of the predetermined time period in step 136, the atrial defibrillator 30, and more specifically the charge delivery and energy control 72, withholds the application of the cardioverting electrical energy and restarts the entire sequence beginning with step 110. This assures that the atria are not cardioverted at the end of an excessively long cardiac cycle which, as previously mentioned, may be followed by a short cardiac cycle.

As a result of the foregoing, the atrial defibrillator of the present invention provides an alternative approach for precluding the application of cardioverting or defibrillating electrical energy to the atria of the heart in the presence of a possible vulnerable condition. To that end, the atrial defibrillator of the present invention precludes the application of the cardioverting energy at a time when a T wave has not been completed to reduce the risk of inducing ventricular fibrillation during the application of the cardioverting or defibrillating electrical energy to the atria of the heart.

While a particular embodiment of the present invention has been shown and described, modifications may be made. For example, the functions of the T wave detector 51 and R wave detector 52 may be implemented by the microprocessor 60 under operating instructions obtained from the memory 74. As a result, the hardware T wave detector 51 and R wave detectors 51 and 52 respectively may be eliminated.

For software implemented T wave detection, the microprocessor may be implemented for filtering the output of sense amplifier 50 with a high-pass filter at approximately 1.0 Hz and a low-pass filter at approximately 5.0 Hz. The microprocessor then may be implemented to calculate the derivative of the filtered signal using a discrete differentiation of the filtered data and refiltered with a low-pass filter at approximately 5.0 Hz. The detection of the T wave, in accordance with the flow diagram of FIG. 2, begins 100 milliseconds after the initial R wave is detected and continues for 150 milliseconds. The maximum positive and negative slopes may be detected by the microprocessor from the differentiated data in this time interval. The T wave may then be detected as the point between the maximum slopes where the average slope changes to zero or changes sign. To implement the foregoing, a slope averaging technique may be used.

For software implemented R wave detection, the microprocessor may be implemented to filter the output of the R wave detector 52 with a band pass filter characteristic centered at approximately 35 Hz. The microprocessor then calculates the absolute value of the filtered signal. Thereafter, the microprocessor may require four conditions to be met before an R wave is considered to be detected. The first condition is that the absolute value of the filtered signal exceed twice its low-pass (0.1 Hz) filtered value. The second condition is that the absolute value of the filtered signal exceed one-half the average peak values of the last three R waves detected. The third condition is that the absolute value of the filtered signal must exceed a value set by the following relationship:

$$V_{th} = V_{last} * e^{-t/200ms}$$

where $V_{last}$ is the peak of the absolute value of the last R wave detected and t is the time since the last R wave. Lastly, the fourth condition is that the time since the last R wave cannot be less than 150 milliseconds. When all four of these conditions are met, the microprocessor then may consider an R wave to have been detected.

As a further modification, steps 110, 112, 114, 118, and 120 may be eliminated such that the precardioversion interval timing process begins with step 116 as illustrated in FIG. 2. In accordance with this modified embodiment, if an R wave is detected before the completion of the predetermined delay time, the microprocessor would then return to step 116 to detect for a further T wave.

Lastly, the T wave detection and interval timing of the present invention may be utilized to advantage in an external atrial defibrillator wherein an electrode or electrodes adhered to the surface of the skin of a patient are employed along with R wave and T wave detectors for detecting R waves and T waves, and surface pad electrodes are utilized for applying the cardioverting electrical energy to the atria of the heart. Such surface detecting and pad electrodes are well known in the art. Hence, it is therefore intended in the appended claims to cover all such changes and modifications which fall within the true spirit and scope of the invention.

What is claimed is:

1. An atrial defibrillator for providing cardioverting electrical energy to the atria of a human heart, said atrial defibrillator comprising:

detecting means for detecting R waves and T waves of the heart;

cardioverting means responsive to said detecting means for applying said cardioverting electrical energy to the atria of the heart after a T wave is detected by said detecting means and in timed relation to an R wave detected by said detecting means after said detected T wave is completed, said R wave detected after said detected T wave is completed being the first R wave detected after said detected T wave;

timing means responsive to said detecting means for timing a predetermined delay time upon the detection of said detected T wave, said cardioverting means being responsive to said timing means for applying said cardioverting electrical energy to the atria of the heart after said timing means has timed said predetermined delay time and in timed relation to said R wave detected after said detected T wave, wherein said timing means times a predetermined time period after said predetermined delay time and wherein said cardioverting means is responsive to said timing means for withholding the application of said cardioverting electrical energy when the timing of said predetermined time period is completed before an R wave is detected, and wherein said timing means is responsive to said detecting means detecting an initial R wave for timing a first predetermined time period and wherein said timing means only times said predetermined delay time when said detected T wave is detected within said first predetermined time period.

2. An atrial defibrillator as defined in claim 1 wherein said timing means is responsive to said detecting means detecting an R wave within said first predetermined time period for retiming said first predetermined time period.

3. An atrial defibrillator as defined in claim 1 wherein said timing means is responsive to said detecting means detecting an R wave within said predetermined delay time for retiming said first predetermined time period.

4. An atrial defibrillator as defined in claim 1 wherein said detecting means is responsive to said timing means completing the timing of said first predetermined time period without a T wave being detected to detect for a further initial R wave.

5. An atrial defibrillator as defined in claim 1 wherein said detecting means is responsive to said timing means and to detecting a further T wave during said predetermined delay time to detect for a further initial R wave.

6. An atrial defibrillator as defined in claim 1 wherein said detecting means is responsive to detecting a further T wave before detecting said first R wave to detect for a further initial R wave.

7. An atrial defibrillator as defined in claim 1 wherein said detecting means is responsive to said timing means completing the timing of said predetermined time period without said detecting means detecting said first R wave to detect for a further initial R wave.

8. An implantable atrial defibrillator for providing cardioverting electrical energy to the atria of a human heart in need of cardioversion, said atrial defibrillator comprising:
first detecting means for detecting R waves of the heart;
second detecting means for detecting T waves of the heart;
third detecting means for detecting atrial activity of the heart;
atrial fibrillation detecting means responsive to said third detecting means for determining when the atria of the heart are in need of cardioversion; and
cardioverting means for applying said cardioverting electrical energy to the atria of the heart when the atria of the heart are in need of cardioversion, after said second detecting means detects a T wave, and in timed relation to an R wave detected by said first detecting means after said detected T wave is completed, said R wave detected after said detected T wave is completed being the first R wave detected by said first detecting means after said detected T wave.

9. An atrial defibrillator as defined in claim 8 wherein said cardioverting means applies said cardioverting electrical energy in synchronism with said first R wave detected after said detected T wave.

10. An atrial defibrillator as defined in claim 8 further including timing means responsive to said second detecting means for timing a predetermined delay time upon the detection of said detected T wave and wherein said cardioverting means is further responsive to said timing means for applying said cardioverting electrical energy to the atria of the heart after said timing means has timed said predetermined delay time and in timed relation to said R wave detected after said detected T wave.

11. An atrial defibrillator as defined in claim 10 wherein said timing means times a predetermined time period after said predetermined delay time and wherein said cardioverting means is responsive to said timing means for withholding the application of said cardioverting electrical energy when the timing of said predetermined time period is completed before an R wave is detected by said first detecting means.

12. An atrial defibrillator as defined in claim 11 wherein said timing means is responsive to said first detecting means detecting an initial R wave for timing a first predetermined time period and wherein said timing means only times said predetermined delay time when said detected T wave is detected within said first predetermined time period.

13. An atrial defibrillator as defined in claim 12 wherein said timing means is responsive to said first detecting means detecting an R wave within said first predetermined time period for retiming said first predetermined time period.

14. An atrial defibrillator as defined in claim 12 wherein said timing means is responsive to said first detecting means detecting an R wave within said predetermined delay time for retiming said first predetermined time period.

15. An atrial defibrillator as defined in claim 12 wherein said first detecting means is responsive to said timing means completing the timing of said first predetermined time period without a T wave being detected to detect for a further initial R wave.

16. An atrial defibrillator as defined in claim 12 wherein said first detecting means is responsive to said timing means and to said second detecting means detecting a further T wave during said predetermined delay time to detect for a further initial R wave.

17. An atrial defibrillator as defined in claim 12 wherein said first detecting means is responsive to said second detecting means detecting a further T wave before detecting said first R wave to detect for a further initial R wave.

18. An atrial defibrillator as defined in claim 12 wherein said first detecting means is responsive to said timing means completing the timing of said predetermined time period without said first detecting means detecting said first R wave to detect for a further initial R wave.

19. A method of applying cardioverting electrical energy to the atria of a human heart in need of cardioversion, said method including the steps of:
detecting T waves of the heart;
detecting R waves of the heart;
timing a predetermined delay time upon detecting a T wave;
applying said cardioverting electrical energy to the atria of the heart after timing said predetermined delay time and in timed relation to the first R wave detected following a detected and completed T wave;

timing a predetermined time period after said predetermined delay time and withholding the application of said cardioverting electrical energy if the timing of said predetermined time period is completed before detecting an R wave; and timing a first predetermined time period upon detecting an initial R wave and timing said predetermined delay time only if said detected T wave is detected within said first predetermined time period.

20. A method as defined in claim 19 including the further step of retiming said first predetermined time period if an R wave is detected within said first predetermined time period.

21. A method as defined in claim 19 including the further step of retiming said first predetermined time period if an R wave is detected within said predetermined delay time.

22. A method as defined in claim 19 including the further step of detecting for a further initial R wave if the timing of said first predetermined time period is completed without detecting a T wave.

23. A method as defined in claim 19 including the further step of detecting for a further initial R wave if a further T wave is detected during said predetermined delay time.

24. A method as defined in claim 19 including the further step of detecting for a further initial R wave upon detecting a further T wave before detecting said first R wave.

25. A method as defined in claim 19 including the further step of detecting for a further initial R wave upon completing the timing of said predetermined time period without detecting said first R wave.

26. A method of providing cardioverting electrical energy to the atria of a human heart in need of cardioversion, said method comprising:
    detecting R waves of the heart;
    detecting T waves of the heart;
    detecting atrial activity of the heart;
    determining from the detected atrial activity when the atria of the heart are in need of cardioversion; and
    applying said cardioverting electrical energy to the atria of the heart when the atria of the heart are in need of cardioversion, after detecting a T wave, and in timed relation to an R wave detected after said detected T wave is completed, said R wave detected after said detected T wave is completed being the first R wave detected after said detected T wave.

* * * * *